US011733195B2

(12) United States Patent
Wu

(10) Patent No.: US 11,733,195 B2
(45) Date of Patent: Aug. 22, 2023

(54) ELECTROCHEMICAL SENSOR FOR HUMORAL DETECTION AND DETECTION DEVICE

(71) Applicant: BOE TECHNOLOGY GROUP CO., LTD., Beijing (CN)

(72) Inventor: Zheng Wu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 890 days.

(21) Appl. No.: 16/605,021

(22) PCT Filed: Sep. 29, 2018

(86) PCT No.: PCT/CN2018/108648
§ 371 (c)(1),
(2) Date: Oct. 14, 2019

(87) PCT Pub. No.: WO2020/062143
PCT Pub. Date: Apr. 2, 2020

(65) Prior Publication Data
US 2021/0325332 A1   Oct. 21, 2021

(51) Int. Cl.
*A61B 10/00* (2006.01)
*G01N 27/30* (2006.01)
(Continued)

(52) U.S. Cl.
CPC .......... *G01N 27/301* (2013.01); *A61B 5/682* (2013.01); *A61B 10/0051* (2013.01);
(Continued)

(58) Field of Classification Search
None
See application file for complete search history.

(56) References Cited

U.S. PATENT DOCUMENTS

| 6,923,894 B2 * | 8/2005 | Huang ................... C12Q 1/002 204/403.05 |
| 2003/0098234 A1 * | 5/2003 | Hasegawa .............. C12Q 1/005 204/403.04 |

(Continued)

FOREIGN PATENT DOCUMENTS

| CN | 105606682 A | 5/2016 |
| CN | 106104264 A | 11/2016 |

(Continued)

OTHER PUBLICATIONS

European Search report issued for EP Application No. 18927226.3, dated Mar. 24, 2022, 11 pages.

*Primary Examiner* — Alex M Valvis
*Assistant Examiner* — Aurelie H Tu
(74) *Attorney, Agent, or Firm* — Dave Law Group LLC; Raj S. Dave

(57) ABSTRACT

An electrochemical sensor for humoral detection and a detection device. The electrochemical sensor for humoral detection includes a material layer including at least one hydrophilic region; and at least one detection unit, located in the hydrophilic region. The hydrophilic region includes a sampling port configured to be in contact with a liquid sample (for example, saliva) to be detected, the detection unit includes a working electrode and an opposed electrode disposed apart from each other, the working electrode comprises a reaction surface containing a substance configured to have a reaction with an analyte in the liquid sample, and the working electrode and the opposed electrode are configured to detect an electrical signal generated by the reaction so as to detect the analyte.

13 Claims, 3 Drawing Sheets

(51) Int. Cl.
*G01N 27/401* (2006.01)
*G01N 33/543* (2006.01)
*A61B 5/00* (2006.01)
*H01M 8/16* (2006.01)
*G01N 27/327* (2006.01)

(52) U.S. Cl.
CPC ....... *G01N 27/3271* (2013.01); *G01N 27/401* (2013.01); *G01N 33/5438* (2013.01); *H01M 8/16* (2013.01); *A61B 2562/02* (2013.01); *A61B 2562/16* (2013.01)

(56) References Cited

U.S. PATENT DOCUMENTS

| | | | | |
|---|---|---|---|---|
| 2004/0238358 | A1* | 12/2004 | Forrow | C12Q 1/001 204/403.01 |
| 2006/0004272 | A1* | 1/2006 | Shah | G01N 33/5438 600/365 |
| 2007/0078307 | A1* | 4/2007 | Debreczeny | G01N 31/223 600/309 |
| 2007/0169533 | A1* | 7/2007 | Shah | A61B 5/14532 73/1.01 |
| 2010/0169035 | A1* | 7/2010 | Liang | A61B 5/14865 702/65 |
| 2016/0338626 | A1 | 11/2016 | Wang et al. | |
| 2017/0265789 | A1 | 9/2017 | Naseri et al. | |
| 2018/0104694 | A1 | 4/2018 | Huff et al. | |
| 2020/0268293 | A1 | 8/2020 | Gassler et al. | |

FOREIGN PATENT DOCUMENTS

| | | |
|---|---|---|
| CN | 107096581 A | 8/2017 |
| EP | 2075339 A1 | 7/2009 |
| EP | 3687385 A1 | 8/2020 |
| WO | 2013130145 A2 | 9/2013 |

\* cited by examiner

ELECTROCHEMICAL SENSOR FOR HUMORAL DETECTION AND DETECTION DEVICE

CROSS-REFERENCE

The present application is the U.S. national stage of International Patent Application No. PCT/CN2018/108648, Sep. 29, 2018, the entire disclosure of which is incorporated herein by reference as part of the present application.

TECHNICAL FIELD

Embodiments of the present disclosure relate to an electrochemical sensor for humoral detection and a detection device.

BACKGROUND

With continuous development of science and technology, people have continuously increased requirements on quick and timely biochemical detection, accordingly. Therefore, highly effective and reliable detection methods and devices have gradually become the hotspot of current research and the focus in the market.

Electrochemical sensor is a kind of sensor which obtains information of an analyte of a sample, such as an ingredient and a concentration of the analyte, by detecting an electrical signal generated from a chemical reaction. Generally, the electrochemical sensor can include a working electrode and an opposed electrode which are disposed apart from each other for detecting.

On the other hand, as compared to the detection method and detection device for detecting a sample like blood, the detection method and detection device for detecting a sample obtained non-intrusively, such as tear, sweat and saliva, possess a better application prospect and a wider application range in the market.

SUMMARY

At least one embodiment of the present disclosure provides an electrochemical sensor for humoral detection, including: a material layer including at least one hydrophilic region; and at least one detection unit located in the hydrophilic region; the hydrophilic region includes a sampling port configured to be in contact with a liquid sample to be detected; the detection unit includes a working electrode and an opposed electrode disposed apart from each other; the working electrode includes a reaction surface containing a substance configured to have a chemical reaction with an analyte in the liquid sample; the working electrode and the opposed electrode are configured to detect an electrical signal generated by the chemical reaction so as to detect the analyte.

For example, in the electrochemical sensor for humoral detection provided by an embodiment of the present disclosure, the at least one hydrophilic region includes a plurality of hydrophilic regions, and the material layer further includes a lyophobic region disposed among adjacent ones of the plurality of hydrophilic regions to separate different ones of the plurality of hydrophilic regions from each other.

For example, the electrochemical sensor for humoral detection provided by an embodiment of the present disclosure further includes a lyophobic substrate, and the material layer is on the lyophobic substrate.

For example, in the electrochemical sensor for humoral detection provided by an embodiment of the present disclosure, the at least one hydrophilic region includes a plurality of hydrophilic regions, and the plurality of hydrophilic regions are disposed apart from each other on the lyophobic substrate.

For example, in the electrochemical sensor for humoral detection provided by an embodiment of the present disclosure, the material layer includes a paper material layer.

For example, in the electrochemical sensor for humoral detection provided by an embodiment of the present disclosure, the paper material layer includes filter paper or nano-paper.

For example, in the electrochemical sensor for humoral detection provided by an embodiment of the present disclosure, the paper material layer includes a nano-paper; the hydrophilic region includes a nano-cellulose; and the lyophobic region includes a nano-cellulose having a surface adsorbed with a polysaccharide molecule.

For example, the electrochemical sensor for humoral detection provided by an embodiment of the present disclosure further includes a lyophobic layer located at a side of the material layer away from the detection unit.

For example, in the electrochemical sensor for humoral detection provided by an embodiment of the present disclosure, the detection unit is disposed on a corresponding hydrophilic region, and the reaction surface is in contact with the material layer.

For example, in the electrochemical sensor for humoral detection provided by an embodiment of the present disclosure, a planar shape of the hydrophilic region is a water drop shape, and the sampling port is located at a tip portion of the water drop shape.

For example, the electrochemical sensor for humoral detection provided by an embodiment of the present disclosure further includes a protection layer located on the sampling port, and the protection layer includes a lyophobic material.

For example, in the electrochemical sensor for humoral detection provided by an embodiment of the present disclosure, the liquid sample includes saliva, and the substance includes glucose oxidase.

For example, in the electrochemical sensor for humoral detection provided by an embodiment of the present disclosure, the reaction surface further includes a glucose oxidase immobilization material, and the glucose oxidase immobilization material includes ferrocene, glutaraldehyde and bovine serum albumin.

For example, in the electrochemical sensor for humoral detection provided by an embodiment of the present disclosure, the detection unit further includes a reference electrode located between the working electrode and the opposed electrode.

For example, the electrochemical sensor for humoral detection provided by an embodiment of the present disclosure further includes a driving circuit connected with the working electrode and the opposed electrode respectively and configured to drive the working electrode and the opposed electrode to perform detection.

For example, in the electrochemical sensor for humoral detection provided by an embodiment of the present disclosure, the driving circuit includes a signal modulation circuit configured to amplify an electrical signal detected by the working electrode and the opposed electrode.

At least one embodiment of the present disclosure further provides a detection device, including any of the electrochemical sensors for humoral detection described above.

For example, the detection device provided by an embodiment of the present disclosure further includes: a sample collecting device configured to acquire the liquid sample; and a biological fuel cell configured to utilize the liquid sample to generate electricity; the sample collecting device includes a sample tank, a biological fuel cell tank and a valve connected with the sample tank and the biological fuel cell tank respectively; and the biological fuel cell is disposed in the biological fuel cell tank.

For example, in the detection device provided by an embodiment of the present disclosure, the sample tank is provided with a detector communicated with the valve; the detector is configured to detect an amount of the liquid sample in the sample tank, and control the valve to cause the liquid sample to flow into the biological fuel cell tank upon the amount of the liquid sample exceeding a predetermined value.

For example, in the detection device provided by an embodiment of the present disclosure, the detector includes at least one selected from the group consisting of a pressure sensor, a humidity sensor and a liquid level height sensor.

For example, in the detection device provided by an embodiment of the present disclosure, the biological fuel cell includes an output terminal, and the output terminal is connected with the electrochemical sensor for humoral detection so as to power the electrochemical sensor for humoral detection.

For example, in the detection device provided by an embodiment of the present disclosure, the sample tank includes a notch, and a size of the notch is greater than a size of the sampling port so that the sampling port is capable of protruding into the notch.

For example, in the detection device provided by an embodiment of the present disclosure, the sample collecting device includes: an outer sidewall; an inner sidewall; and a bottom connecting the outer sidewall with the inner sidewall to form a tooth socket; depths of two ends of the tooth socket away from the sample tank is smaller than a depth of a portion of the tooth socket close to the sample.

BRIEF DESCRIPTION OF THE DRAWINGS

In order to clearly illustrate the technical solution of embodiments of the present disclosure, the drawings of the embodiments will be briefly described in the following, it is obvious that the drawings in the description are only related to some embodiments of the present disclosure and not limited to the present disclosure.

DETAILED DESCRIPTION

Figure 1:
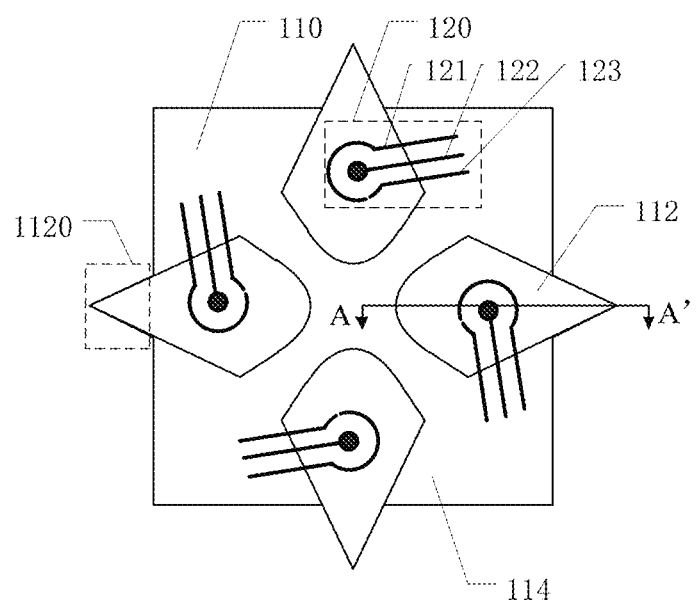
FIG. 1 is a plan view of an electrochemical sensor for humoral detection provided by an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly.

Among the samples obtained in a nonintrusive manner, the saliva, as a kind of continuously regenerated liquid, provides a huge database of "physiological snapshots". Furthermore, using the saliva as a diagnostic specimens is more practical and less error-prone, so as to avoid any pain, anxiety and risk of infection resulted by conventional collecting methods (e.g., blood sampling or tissue biopsy) of intrusive samples (e.g., blood). Moreover, saliva can be used for detecting items such as individual hormones, stress and metabolic status, and hence is applicable for early diagnosis and treatment of disease, so as to effectively mitigate the severity of illness and play an important role in treating potential complications. On the other hand, the conventional electrochemical sensor for humoral detection is expensive, inconvenient to carry, difficult for reutilization, and cannot enter daily lives of ordinary consumers, which limits application scenarios of the electrochemical sensor for humoral detection.

Therefore, an embodiment of the present disclosure provides an electrochemical sensor for humoral detection and a detection device, which can utilize saliva for biochemical detection. The electrochemical sensor for humoral detection includes a material layer and at least one detection unit. The material layer includes at least one hydrophilic region, and the at least one detection unit is located in the hydrophilic region. The hydrophilic region includes a sampling port configured to be in contact with a liquid sample (e.g., saliva) to be detected; the detection unit includes a working electrode and an opposed electrode disposed apart from each other; the working electrode includes a reaction surface containing a substance configured to have a chemical reaction with an analyte in the liquid sample; the working electrode and the opposed electrode are configured to detect an electrical signal generated from the chemical reaction so as to detect the analyte. The electrochemical sensor for humoral detection can absorb the liquid sample and convey the liquid sample to a correspondingly disposed detection unit through capillary action by utilizing a hydrophilicity of the hydrophilic region in the material layer, and then the detection unit can achieve detecting the analyte in the liquid sample through the substance on the working electrode having a chemical reaction with the analyte in the liquid sample. The electrochemical sensor for humoral detection has a simple structure and can fabricate the material layer by adopting a paper-based material, so as to reduce costs of the electrochemical sensor for humoral detection, and to facilitate portability, thereby facilitating the promotion and application of products in a better way.

Hereinafter, the electrochemical sensor for humoral detection and the detection device provided by the embodiments of the present disclosure will be described in details with reference to the drawings.

An embodiment of the present disclosure provides an electrochemical sensor for humoral detection. FIG. 1 is a plan view of an electrochemical sensor for humoral detection provided by an embodiment of the present disclosure. As illustrated in FIG. 1, the electrochemical sensor for humoral detection includes a material layer 110 and at least one detection unit 120 located on the material layer 110. The material layer 110 includes at least one hydrophilic region 112; the at least one hydrophilic region 112 is disposed in one-to-one correspondence with the at least one detection unit 120. For example, when the number of the hydrophilic region 112 and the number of the detection unit 120 both are one, the detection unit 120 is disposed in the hydrophilic region 112; when the number of the hydrophilic region 112 and the number of the detection unit 120 both are plural, each of the hydrophilic regions 112 is disposed in correspondence with one of the detection units 120. The hydrophilic region 112 includes a sampling port 1120 configured to be in contact with a liquid sample (e.g., saliva) to be detected; the detection unit 120 includes a working electrode 121 and an opposed electrode 122 disposed apart from each other; the working electrode 121 includes a reaction surface containing a substrate which has a chemical reaction with an analyte in the liquid sample; the working electrode 121 and the opposed electrode 122 are configured to detect an electrical signal generated from the chemical reaction.

For example, the above-described substance can be a catalyst or a reactant corresponding to the analyte.

In the electrochemical sensor for humoral detection provided by the present embodiment, the hydrophilicity of the hydrophilic region 112 in the material layer 110 allows to absorb the liquid sample and convey the liquid sample to a correspondingly disposed detection unit 120 through capillary action; at this time, the detection unit 120 can have a chemical reaction with the analyte in the liquid sample by utilizing the substance on the reaction surface of the working electrode 121, and then obtain information of the analyte such as the type and the concentration of the analyte by detecting the electrical signal generated from the chemical reaction through the working electrode 121 and the opposed electrode 112, so as to achieve detecting the analyte in the liquid sample. The electrochemical sensor for humoral detection has a simple structure and can fabricate the material layer by adopting a paper-based material, so as to reduce costs of the electrochemical sensor for humoral detection, and to facilitate portability, thereby facilitating the promotion and application of products in a better way.

For instance, in some examples, the above-described liquid sample can include saliva, and the above-described substance includes glucose oxidase. Because the glucose oxidase can catalyze the glucose in the saliva to be oxidized, the electrochemical sensor for humoral detection can be used for detecting the concentration of the glucose in the saliva.

For instance, in some examples, the reaction surface 1210 can further include a glucose oxidase immobilization material to immobilize the glucose oxidase on the reaction surface. For example, the glucose oxidase immobilization material can include ferrocene, glutaraldehyde and bovine serum albumin. Of course, the embodiment of the present disclosure includes such case but is not limited thereto, and the glucose oxidase immobilization material can also include other substances which can immobilize the glucose oxidase on the reaction surface.

For example, a method of forming a glucose oxidase immobilization material and a glucose oxidase on the reaction surface can include: firstly, placing a prepared working electrode in a supersonic cleaner for cleaning with deionized water for 5 min, then taking out the working electrode for naturally drying; subsequently, coating 5 µL ferrocene ethanol solution with a concentration of 0.1 mol/L, by way of dropping, onto a surface of the prepared working electrode, and drying under room temperature for use later; subsequently, coating 1.5 µL glucose oxidase (GOD) solution with a concentration of 1.5 µL, by way of dropping, onto the surface of the above-described working electrode having been modified by ferrocene, then adding 1 µL bovine serum albumin (BSA) with a mass fraction of 1%, and then adding 1.5 µL glutaraldehyde solution with a mass fraction of 1.5% for cross-linking fixation of enzyme after drying under temperature; finally, removing free enzyme and monomer which are not immobilized by washing using deionized water, then naturally drying under room temperature for film formation, and then storing the film in a refrigerator under a temperature of 4° C. for use later.

For instance, in some examples, as illustrated in FIG. 1, the at least one hydrophilic region 112 includes a plurality of hydrophilic regions 112, that is to say, the material layer 110 includes a plurality of hydrophilic regions 112. In such case, the material layer 110 further includes a lyophobic region 114 disposed among adjacent ones of the plurality of hydrophilic regions 112 to separate different ones of the plurality of hydrophilic regions 112 from each other. In this way, when or after detecting one hydrophilic region 112, the liquid sample in this hydrophilic region 112 is isolated by the lyophobic region and cannot flow into other hydrophilic regions 112 so as to avoid mutual interference and contamination between different hydrophilic regions 112. On the other hand, the lyophobic region 114 can also prevent the liquid sample from overflowing from the hydrophilic region 112 to result in short circuit. It should be explained that, a particular size of the lyophobic region 114 can be configured according to actual conditions; when the lyophobic region is relatively larger, the lyophobic region provides the adjacent hydrophilic region with stronger isolation effect; and when the lyophobic region is relatively smaller, the lyophobic region can reduce an area of the material layer and save a material of the material layer so as to further facilitate reducing the costs and achieving portability.

It should be explained that, because the material layer 110 can be provided with a plurality of hydrophilic regions 112, a plurality of detection units 120 can be provided so as to achieve high integration and further to reduce the costs.

For instance, in some examples, as illustrated in FIG. 1, a planar shape of the hydrophilic region 112 is a water drop shape, and the sampling port 1120 is located at a tip portion of the water drop shape so as to protrude into a tank or a tube for containing the liquid sample. It should be explained that, the above-mentioned tip portion of the water drop shape is a portion corresponding to a rounded portion of the water drop shape. Of course, the present disclosure includes such case but is not limited thereto.

For instance, in some examples, as illustrated in FIG. 1, the detection unit 120 further includes a reference electrode 123 which is disposed apart from the working electrode 121 and apart from the opposed electrode 122. For example, the reference electrode 123 can be configured to monitor an electric potential of the working electrode; in such case, the working electrode 121 and the opposed electrode 122 can form one loop, while the working electrode 121 and the reference electrode 123 can form another loop; the loop formed by the working electrode 121 and the opposed electrode 122 can be configured to measure a current, while the loop formed by the working electrode 121 and the reference electrode 123 can be configured to measure an electric potential at the working electrode. With the usage of the electrochemical sensor for humoral detection, the electric potential at the working electrode 121 would be changed; by determining the electric potential at the working electrode 121 through the reference electrode 123, it can improve the detection accuracy.

For instance, in some examples, a material of the working electrode 121 can include Au, for example, the working electrode can be a lamination of Ni—Cr alloy and Au. A thickness of the Ni—Cr alloy layer can be 10 nm, and a thickness of Au layer can be 100 nm.

For instance, in some examples, the working electrode 121 and the opposed electrode 122 can be fixed on the material layer by a conductive adhesive. In this way, after the usage of the electrochemical sensor for humoral detection, metallic materials such as the working electrode and the opposed electrode can be recycled by removing the material layer.

For instance, in some examples, the material layer 110 includes a paper material; that is to say, the material layer can be made of a paper material. Because the paper material is relatively cheap and is naturally hydrophilic, it has no need of additional process to form a hydrophilic region, so as to reduce the costs of the electrochemical sensor for humoral detection. Moreover, because the paper material is recyclable and degradable, the electrochemical sensor for humoral detection is also recyclable and degradable; as compared with the conventional material layer made of glass material and plastic material, the electrochemical sensor for humoral detection is more environment-friendly. As a result, when the material layer is made of a paper material, the electrochemical sensor for humoral detection has advantages of portability, low costs, recyclability and the like, and hence is suitable for application in remote areas and diagnosis at medical centers. Additionally, because the paper material is recyclable and degradable, it's environment-friendly without producing any digital waste.

Figure 2:
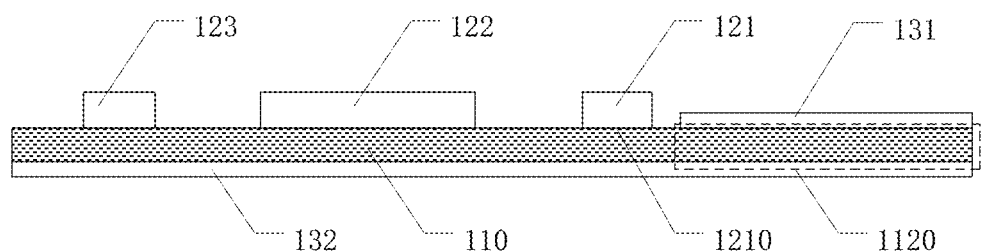
FIG. 2 is a cross-sectional view of an electrochemical sensor for humoral detection provided by an embodiment of the present disclosure taken along AA' direction in FIG. 1.

FIG. 2 is a cross-sectional view of an electrochemical sensor for humoral detection provided by an embodiment of the present disclosure taken along AA' direction in FIG. 1. As illustrated in FIG. 2, the sampling port 1120 can be provided with a protection layer 131 to reduce or eliminate an evaporation of the liquid sample. For example, the protection layer 131 can include an adhesive tape or a thin film.

For instance, in some examples, as illustrated in FIG. 2, the detection unit 120 is disposed on a corresponding hydrophilic region 112, and a reaction surface 1210 is in contact with the material layer 110. Because the liquid sample is absorbed and conveyed to the correspondingly disposed detection unit 120 through the capillary action of the hydrophilic region 112 in the material layer 110, the arrangement of the reaction surface 1210 being in contact with the material layer 110 allows the substance on the reaction surface 1210 to have a chemical reaction with the analyte in the liquid sample. Of course, the embodiment of the present disclosure includes such case but is not limited thereto, and the reaction surface 1210 may not be in contact with the material layer 110; for example, the reaction surface 1210 can be a surface of a side of the working electrode away from the material layer.

For instance, in some examples, as illustrated in FIG. 2, a side of the material layer 110 away from the detection unit 120 is provided with a lyophobic layer 132. On one aspect, the lyophobic layer 132 can reduce the usage of the liquid sample; on the other hand, the lyophobic layer 132 can prevent the liquid sample from wetting a bottom of the electrochemical sensor for humoral detection so as for operation and portability of the user.

For instance, in some examples, the paper material layer can include filter paper or nano-paper.

For example, when the material layer includes filter paper, it has no need of forming the hydrophilic region by an additional process but only needs to perform a lyophobic process to an area on the material layer where the lyophobic region is to be formed, so as to form the above-described hydrophilic region and lyophobic region. Moreover, when the material layer is a filter paper, the above-described protection layer and lyophobic layer can also be formed by performing a lyophobic process to a surface of the paper material layer. For example, the above-descried lyophobic process can include coating a lyophobic material, and the lyophobic material can include paraffin or the like.

For example, when the material layer includes nano-paper, the nano-paper includes nano-cellulose and polysaccharide molecule absorbed on a surface of the nano-cellulose. In the nano-paper, the hydrophilic region can be nano-cellulose, and the lyophobic region can be nano-cellulose modified by the polysaccharide molecule, that is, nano-cellulose having a surface adsorbed with polysaccharide molecule. It should be explained that, the above-mentioned nano-cellulose has a diameter smaller than 100 nm, and the polysaccharide molecule can have an interaction with the nano-cellulose and can be physically absorbed onto the surface of the nano-cellulose so as to reduce the interaction between the nano-cellulose and the polysaccharide molecule, thereby avoiding hygroscopic swelling behavior and resulting in good water resistance. Moreover, in addition to water, humoral fluid (e.g., blood, sweat and the like) further includes many other ingredients, for example, polypeptide, protein, glucose, inorganic salt and the like; as compared with conventional paper-based materials, the nano-paper has more powerful capillary action due to its material property, and allows various ingredients in the humoral fluid sample to be distributed on the nano-paper more uniformly, which facilitates performing the electrochemical detection and achieves improved accuracy. Therefore, using the nano-paper as the material layer also provides better effect of colleting the humoral fluid sample.

For example, a manufacturing method of the lyophobic region in the above-described nano-paper includes: oxidizing a cellulose, and then performing a homogenization treatment to obtain a nano-cellulose; immersing the nano-cellulose in a solution containing a polysaccharide molecule to obtain a processed nano-cellulose; preparing and forming a lyophobic region of the nano-paper by utilizing the above-mentioned processed nano-cellulose. It should be explained that, because the nano-cellulose has been subject to oxidization process, the surface of the nano-cellulose contains a plenty of functional groups such as hydroxyl and carboxyl so as to have an interaction with the polysaccharide molecule, thereby absorbing the polysaccharide molecule.

For example, the above-mentioned polysaccharide molecule is insoluble in water. Considering availability and dispersibility in water, the above-mentioned polysaccharide molecule can be starch or chitosan.

For example, a thickness of the nano-paper is in a range of 30 μm-100 μm, and a roughness of the nano-paper is smaller than 10 nm.

Figure 3:
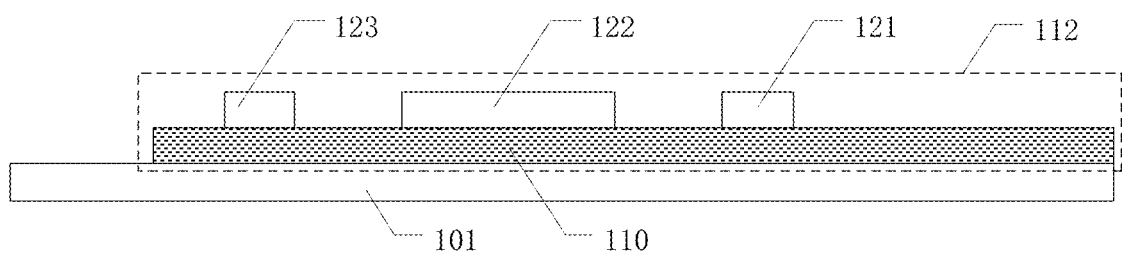
FIG. 3 is a cross-sectional view of another electrochemical sensor for humoral detection provided by an embodiment of the present disclosure taken along AA' direction in FIG. 1.

FIG. 3 is a cross-sectional view of another electrochemical sensor for humoral detection provided by an embodiment of the present disclosure taken along AA' direction in FIG. 1. As illustrated in FIG. 3, the electrochemical sensor for humoral detection further includes a lyophobic substrate 101, and the material layer 110 is disposed on the lyophobic substrate 101. On one aspect, the lyophobic substrate 101 can support the material layer 110; on the other aspect, the lyophobic substrate 101 can prevent the liquid sample from wetting a bottom of the electrochemical sensor for humoral detection so as for operation and portability of the user.

For instance, in some examples, the at least one hydrophilic region 112 includes a plurality of hydrophilic regions 112, and the plurality of hydrophilic regions 112 are disposed apart from each other on the lyophobic substrate 101. In this way, when or after detecting one hydrophilic region 112, the liquid sample in this hydrophilic region 112 is isolated by the lyophobic substrate and cannot flow into other hydrophilic regions 112, so as to avoid mutual interference and contamination between different hydrophilic regions 112.

Figure 4:
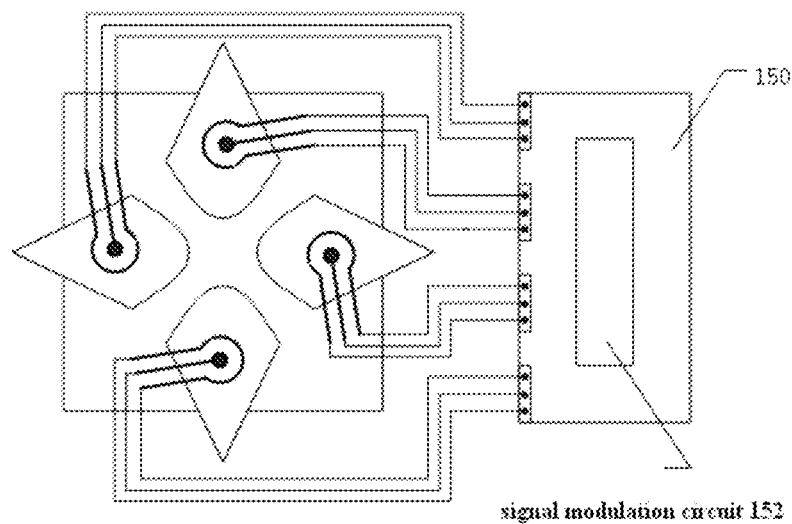
FIG. 4 is a plan view of another electrochemical sensor for humoral detection provided by an embodiment of the present disclosure.

FIG. 4 is a plan view of another electrochemical sensor for humoral detection provided by an embodiment of the present disclosure. As illustrated in FIG. 4, the electrochemical sensor for humoral detection can further include a driving circuit 150 which is connected with the working electrode 121 and the opposed electrode 122 respectively and is configured to drive the working electrode 121 and the opposed electrode 122 to perform detection.

For example, the driving circuit 150 can be disposed on the material layer 110, for example, in the lyophobic region 114 of the material layer 110. Of course, the embodiment of the present disclosure includes such case but is not limited thereto, and the driving circuit 150 may not be disposed on the material layer 110 but is provided separately. It should be explained that, when the driving circuit 150 is disposed on the material layer 110, the driving circuit 150 can be packaged so as to prevent the liquid sample from corroding the driving circuit.

For instance, in some examples, as illustrated in FIG. 4, when the electrochemical sensor for humoral detection includes a plurality of detection units 120, the plurality of detection units 120 are connected to the driving circuit 150 respectively.

For instance, in some examples, the driving circuit 150 can include a signal modulation circuit 152 which is configured to amplify an electrical signal detected by the working electrode 121 and the opposed electrode 122.

Figure 5:
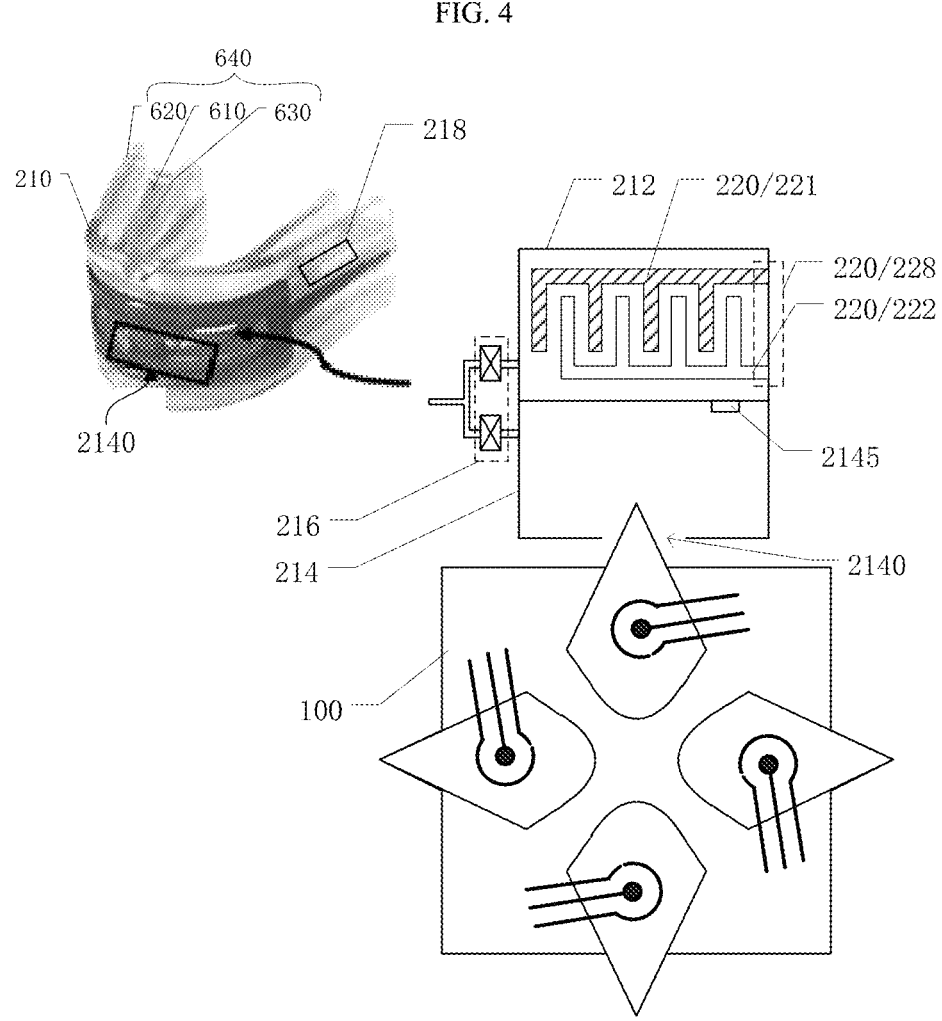
FIG. 5 is a schematic view of a detection device provided by an embodiment of the present disclosure.

An embodiment of the present disclosure provides a detection device. FIG. 5 is a schematic view of a detection device provided by an embodiment of the present disclosure. As illustrated in FIG. 5, the detection device includes an electrochemical sensor 100 for humoral detection, and the electrochemical sensor 100 for humoral detection is the electrochemical sensor for humoral detection provided by any of the examples in the foregoing embodiment.

In the detection device provided by the present embodiment, the hydrophilicity of the hydrophilic region 112 in the material layer 110 of the electrochemical sensor 100 for humoral detection can absorb and convey the liquid sample to a correspondingly disposed detection unit 120 through capillary action; at this time, the detection unit 120 can have a chemical reaction with the analyte in the liquid sample by the substance on the reaction surface 1210 of the working electrode 121, and then obtain information of the analyte such as the type and the concentration of the analyte by detecting the electrical signal generated from the chemical reaction through the working electrode 121 and the opposed electrode 122, so as to achieve detecting the analyte in the liquid sample. The electrochemical sensor for humoral detection has a simple structure and can fabricate the material layer by adopting a paper-based material, so as to reduce costs of the electrochemical sensor for humoral detection, and to facilitate portability, thereby facilitating the promotion and application of products in a better way.

For instance, in some examples, as illustrated in FIG. 5, the detection device further includes: a sample collecting device 210 and a biological fuel cell 220. The sample collecting device 210 can collect a liquid sample; the biological fuel cell 220 can utilize the liquid sample to generate electricity; the sample collecting device 210 includes a biological fuel cell tank 212, a sample tank 214 and a valve 216 connected with the sample tank 214 and the biological fuel cell tank 212 respectively, and the biological fuel cell 220 is disposed in the biological fuel cell tank 212. In this way, the detection device can collect liquid samples through the sample collecting device 210 so that the liquid samples as collected are gathered in the sample tank 214 for detection by the electrochemical sensor 100 for humoral detection. When an amount of the samples in the sample tank 214 reaches a certain value, the valve 216 is controlled to cause the liquid sample to flow into the biological fuel cell tank 212; then the biological fuel cell 220 disposed in the biological fuel cell tank 212 can utilize the liquid sample to generate electricity so as to provide the above-described electrochemical sensor 100 for humoral detection with electric energy. Therefore, the detection device has no need of additionally providing a power supply, and is readily carried and used. Moreover, the biological fuel cell can provide greater energy density (as compared to photovoltaic cell), longer service life and smaller weight (as compared to battery), and can eliminate a risk of chemical leaching of the battery.

For example, the valve 216 can include two sub-valves which are connected with the sample tank 214 and the biological fuel cell tank 212 respectively. When the sub-valve connected with the sample tank 214 is opened while the sub-valve connected with the biological fuel cell tank 212 is closed, the liquid sample can be controlled to flow into the sample tank 214; when the sub-valve connected with the sample tank 214 is closed while the sub-valve connected with the biological fuel cell tank 212 is opened, the liquid sample can be controlled to flow into the biological fuel cell tank 212.

For instance, in some examples, as illustrated in FIG. 5, the sample collecting device 210 can be designed in a form of protective tooth socket in order to collect saliva. For example, the sample collecting device 210 can be placed into a mouth so as to conveniently collect the saliva. The state of the saliva sample would significantly influence the detection result, for example, the amount of saliva as collected is not enough, or the collected saliva contains too many bubbles, or the saliva is contaminated during collection. The sample collecting device 210 provided by the embodiment of the present disclosure can overcome the problems above. For instance, in some examples, as illustrated in FIG. 5, when the sample collecting device 210 is designed as a protective tooth socket, the sample collecting device 210 can include an outer sidewall 620 and an inner sidewall 630 connected through a bottom 610, and a tooth socket 640 is formed by the outer sidewall 620, the inner sidewall 630 and the bottom 610; depths of two ends of the tooth socket 640 away from the sample tank 214 are smaller than a depth of a portion of the tooth socket 640 close to the sample tank 214, so that the bottom 610 of the tooth socket 640 away from both ends of the sample tank 214 has a greater height, which facilitates the saliva flowing into the sample tank.

For instance, in some examples, the sample collecting device 210 can further include an electrical stimulation unit 218 to urge salivary glands to salivate, so as to quicken the collection of the liquid sample. It should be explained that, the above-described electrical stimulation unit 218 also can be powered by the above-described biological fuel cell 220 or by using other power supplies.

For instance, in some examples, as illustrated in FIG. 5, the sample tank 214 is provided with a detector 2145 communicated with the valve 216, and the detector 2145 can detect an amount of liquid sample in the sample tank 214 and control the valve 216 to cause the liquid sample to flow into the biological fuel cell tank 212 for electricity generation upon the amount of liquid sample exceeding a predetermined value. In this way, on one aspect, the amount of sample in the sample tank can be controlled by the detector, so that the amount of humoral liquid absorbed by the electrochemical sensor for humoral detection can be the same every time; on the other aspect, the liquid sample can also flow into the biological fuel cell tank when the amount of liquid sample in the sample tank exceeds the predetermined value.

For example, the above-mentioned communication includes a wireless manner and a wired manner. The wired manner includes a connecting manner by using a wire lead, and the wireless manner includes WiFi, Bluetooth and the like.

For instance, in some examples, the above-described detector can include at least one selected from the group consisting of a pressure sensor, a humidity sensor and a liquid level height sensor. For example, when the detector is a pressure sensor, it can be disposed at a bottom of the sample tank so as to determine an amount of liquid sample in the sample tank by detecting a pressure generated by the liquid sample in the sample tank with respect to the detector; when the detector is a humidity sensor, it can be disposed at a top of the sample tank so as to determine the amount of liquid sample in the sample tank by detecting a humidity in the sample tank; when the detector is a liquid level height sensor, the amount of liquid sample in the sample tank can be determined directly by detecting a height of liquid level of the liquid sample in the sample tank.

For instance, in some examples, the sample collecting device includes a guide channel (not illustrated) configured to guide the liquid sample as collected into the above-described biological fuel cell tank. The particular position and shape of the guide channel can be designed according to actual conditions, and the embodiment of the present disclosure is not limited thereto. For instance, in some examples, as illustrated in FIG. 5, the biological fuel cell 220 includes an output terminal 228, and the output terminal 228 can be connected with the electrochemical sensor 100 for humoral detection so as to power the electrochemical sensor 100 for humoral detection.

For instance, in some examples, as illustrated in FIG. 5, the sample tank 214 includes a notch 2140, and a size of the notch 2140 is greater than a size of the sampling port 1120 so that the sampling port 1120 is capable of protruding into the notch 2140 to absorb the liquid sample.

It should be explained that, when the electrochemical sensor 100 for humoral detection includes a plurality of detection units, liquid samples collected by a plurality of sample collecting devices can be detected by one and the same electrochemical sensor 100 for humoral detection, so as to considerably improve the efficiency and save the cost.

Figure 6:
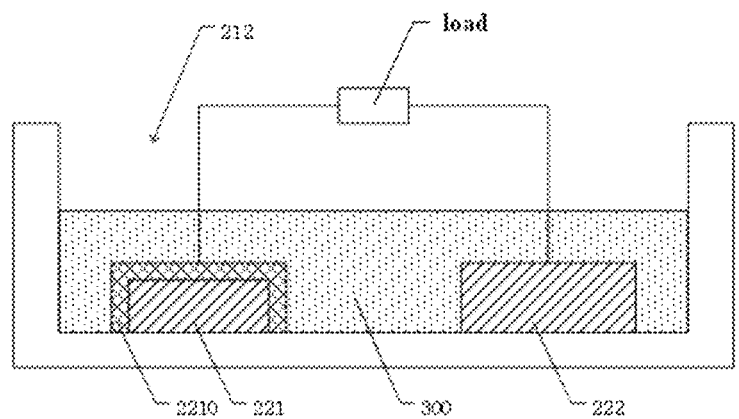
FIG. 6 is a working diagram of a biological fuel cell provided by an embodiment of the present disclosure.

FIG. 6 is a cross-sectional view of a biological fuel cell provided by an embodiment of the present disclosure. As illustrated in FIG. 5 and FIG. 6, the biological fuel cell 220 includes an anode 221 and a cathode 222.

For example, when the liquid sample 300 is saliva, the anode 221 includes a catalyst 2210 so as to convert a biological fuel substance in the saliva into an oxidation product during an oxidation process which releases an electron. During a chemical reduction, at the cathode 222, the biological fuel substance obtains the electron and is reduced, so as to generate current by this process.

Figure 7:
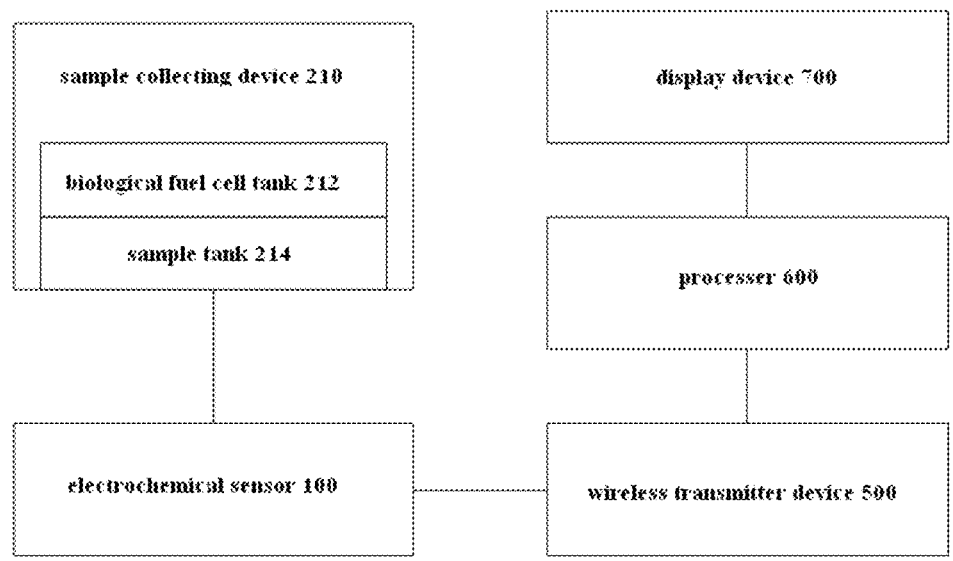
FIG. 7 is a schematic view of another detection device provided by an embodiment of the present disclosure.

FIG. 7 is a schematic view of another detection device provided by an embodiment of the present disclosure. As illustrated in FIG. 7, the detection device can further include a wireless transmitter device 500 configured to transmit data detected by the electrochemical sensor 100 for humoral detection, for example, transmitting the data to a processer for processing.

For instance, in some examples, the detection device can further include a display device 700 and a processor 600; the detection device can process the data detected by the electrochemical sensor 100 for humoral detection through the processer 600, and can display a detection result through the display device 700.

For example, the display device can be a liquid crystal display device, an organic light-emitting diode display device, an electronic paper display device and the like.

For example, the display device can be a wearable display device which can be worn on a user, so that the user can perform detection anytime and anywhere and can obtain the detection result through the wearable display device.

The following statements should be noted:

(1) The accompanying drawings involve only the structure(s) in connection with the embodiment(s) of the present disclosure, and other structure(s) can be referred to common design(s).

(2) In case of no conflict, features in one embodiment or in different embodiments can be combined.

What have been described above are only specific implementations of the present disclosure, the protection scope of the present disclosure is not limited thereto, the protection scope of the present disclosure should be based on the protection scope of the claims.

What is claimed is:

1. An electrochemical sensor for humoral detection, comprising:
   a material layer comprising a plurality of hydrophilic regions; and
   a plurality of detection units located on the material layer, each of the plurality of hydrophilic regions is provided with a corresponding one of the plurality of detection units, respectively, wherein each of the plurality of hydrophilic regions comprises a sampling port configured to be in contact with a liquid sample to be detected, each of the plurality of detection units comprises a working electrode and an opposed electrode disposed apart from each other, the working electrode comprises a reaction surface containing a substance configured to have a reaction with an analyte in the liquid sample, and the working electrode and the opposed electrode are configured to detect an electrical signal generated by the reaction so as to detect the analyte, wherein the material layer further comprises a lyophobic region disposed among adjacent ones of the plurality of hydrophilic regions to separate different ones of the plurality of hydrophilic regions from each other; and a nano-paper;

each of the plurality of hydrophilic regions comprises a nano-cellulose, and the lyophobic region comprises a nano-cellulose having a surface adsorbed with a polysaccharide molecule.

2. An electrochemical sensor for humoral detection, comprising:

a material layer comprising a plurality of hydrophilic regions; and a plurality of detection units located on the material layer, each of the plurality of hydrophilic regions is provided with a corresponding one of the plurality of detection units, respectively, wherein each of the plurality of hydrophilic regions comprises a sampling port configured to be in contact with a liquid sample to be detected, each of the plurality of detection units comprises a working electrode and an opposed electrode disposed apart from each other, the working electrode comprises a reaction surface containing a substance configured to have a reaction with an analyte in the liquid sample, and the working electrode and the opposed electrode are configured to detect an electrical signal generated by the reaction so as to detect the analyte, wherein a planar shape of each the hydrophilic region is a water drop shape, and the sampling port is located at a tip portion of the water drop shape.

3. The electrochemical sensor for humoral detection according to claim 2, wherein the material layer further comprises a lyophobic region disposed among adjacent ones of the plurality of hydrophilic regions to separate different ones of the plurality of hydrophilic regions from each other.

4. The electrochemical sensor for humoral detection according to claim 3, further comprising:

a lyophobic layer, located at a side of the material layer away from the plurality of detection units.

5. The electrochemical sensor for humoral detection according to claim 2, further comprising:

a lyophobic substrate, wherein the material layer is on the lyophobic substrate.

6. The electrochemical sensor for humoral detection according to claim 5, wherein the plurality of hydrophilic regions are disposed apart from each other on the lyophobic substrate.

7. The electrochemical sensor for humoral detection according to claim 2, wherein the material layer comprises a paper material.

8. The electrochemical sensor for humoral detection according to claim 7, wherein the paper material comprises filter paper or nano-paper.

9. The electrochemical sensor for humoral detection according to claim 2, wherein each detection unit is disposed in a corresponding hydrophilic region, and the reaction surface is in contact with the material layer.

10. The electrochemical sensor for humoral detection according to claim 2, further comprising:

a protection layer located on the sampling port,
wherein the protection layer comprises a lyophobic material.

11. The electrochemical sensor for humoral detection according to claim 2, wherein the liquid sample comprises saliva, and the substance comprises glucose oxidase.

12. The electrochemical sensor for humoral detection according to claim 2, wherein each detection unit further comprises: a reference electrode located between the working electrode and the opposed electrode.

13. The electrochemical sensor for humoral detection according to claim 2, further comprising:

a driving circuit connected with the working electrode and the opposed electrode respectively and configured to drive the working electrode and the opposed electrode to perform detection.

* * * * *